US010058363B2

(12) United States Patent
Burke et al.

(10) Patent No.: US 10,058,363 B2
(45) Date of Patent: Aug. 28, 2018

(54) RIB FIXATION SYSTEM

(71) Applicants: Shawn M. Burke, Atlantic Beach, FL (US); Travis Simpson, Atlantic Beach, FL (US); Rich McLaughlin, Jacksonville Beach, FL (US); Axel Waizenegger, Muhlheim (DE); Daniel Grimm, Bottingen (DE); Thomas Koett, Kolbingen (DE)

(72) Inventors: Shawn M. Burke, Atlantic Beach, FL (US); Travis Simpson, Atlantic Beach, FL (US); Rich McLaughlin, Jacksonville Beach, FL (US); Axel Waizenegger, Muhlheim (DE); Daniel Grimm, Bottingen (DE); Thomas Koett, Kolbingen (DE)

(73) Assignee: KARL LEIBINGER MEDIZINTECHNIK GMBH & CO KG, Muehlheim (DE)

( * ) Notice: Subject to any disclaimer, the term of this patent is extended or adjusted under 35 U.S.C. 154(b) by 204 days.

(21) Appl. No.: 14/846,908

(22) Filed: Sep. 7, 2015

(65) Prior Publication Data

US 2017/0065317 A1 Mar. 9, 2017

(51) Int. Cl.
*A61B 17/80* (2006.01)

(52) U.S. Cl.
CPC ...... *A61B 17/8076* (2013.01); *A61B 17/8085* (2013.01)

(58) Field of Classification Search
CPC .. A61B 17/885; A61B 17/8076; A61B 17/823
USPC ............. 606/70, 71, 280–299, 902–906
See application file for complete search history.

(56) References Cited

U.S. PATENT DOCUMENTS

| 6,786,909 | B1* | 9/2004 | Dransfeld | A61B 17/8052 606/280 |
| 2002/0143336 | A1* | 10/2002 | Hearn | A61B 17/8009 606/246 |
| 2006/0235408 | A1* | 10/2006 | Wang | A61B 17/663 606/281 |
| 2009/0318920 | A1* | 12/2009 | Jacobs | A61B 17/8071 606/70 |
| 2014/0039563 | A1* | 2/2014 | Mocanu | A61B 17/8057 606/291 |
| 2015/0018830 | A1* | 1/2015 | Knoepfle | A61B 17/8076 606/71 |

* cited by examiner

*Primary Examiner* — Matthew Lawson
(74) *Attorney, Agent, or Firm* — Thomas C. Saitta

(57) ABSTRACT

A rib fixation system having a bone plate and mono-cortical bone screws adapted for affixation to a rib, the security of the system being enhanced by providing paired sets of screw-receiving openings, wherein the offset axis of each opening of the paired set is approximately ten degrees off from the normal axis in the transverse direction toward the longitudinal midline of the bone plate and is also approximately ten degrees off the normal axis in the longitudinal direction, with the offset axis of each opening in a paired set being turned toward the other opening in the paired set.

10 Claims, 7 Drawing Sheets

RIB FIXATION SYSTEM

BACKGROUND OF THE INVENTION

This invention relates generally to the field of bone fixation, wherein rigid bone plates are affixed to weak, fractured or damaged bones to stabilize, secure and strengthen the bone, typically using mechanical fasteners inserted into the bone to attach the plate to the bone.

The use of rigid bone plates to stabilize weak, damaged or fractured bones is well known, the plates having openings or bores through which bone screws or similar mechanical fasteners are inserted, the bone screws being driven into the bone to secure the bone or bone fragments to the plate. The plates are typically made of rigid metal, and often are constructed of material with sufficient malleability to allow the surgeon to bend or twist the plate in order to optimize the shape or contour of the plate for better conformation to the bone surface.

The fixation of bone plates to small and thin bones, such as for example a rib, presents problems not encountered with larger and thicker bones. One significant problem is the lack of sufficient bone material to achieve secure fixation of the plate to the bone, since the size and/or length of the bone screws may need to be reduced. Another problem may arise if the bone material is inherently weak, such that the bone screws may have a tendency to work loose over time. Another problem in some known systems is that often the bone screws are all oriented perpendicularly to the surface of the bone with their axes in parallel, which may result in gradual separation of the bone and plate.

Rib bones are elongated, curved and thin with a relatively thin cortex (the outer layer of the bone), which presents significant challenges for affixation of bone plates. In many cases short mono-cortical bone screws are not suitable and bi-cortical bone screws are utilized in order to provide sufficiently secure the bone plate to the rib bone, the bone screws passing through both the anterior and the posterior portions of the cortex. Obviously it is not beneficial to have the sharp tips of the bone screws passing through the rib and extending form the posterior cortex into the body cavity.

It is an object of this invention to provide a rib fixation system comprising a bone plate and mono-cortical bone screws that addresses the problems set forth above, wherein bone screws passing only through the anterior cortex provide sufficient affixation of the bone plate to the rib, the security of the system being enhanced by providing paired sets of screw-receiving openings, wherein the axis of each of the bores of the openings in a paired set are offset from the axis normal to the surface of the bone plate, and further wherein the offset axis of each opening of the paired set is approximately ten degrees off from the normal axis in the transverse direction toward the longitudinal midline of the bone plate and is also approximately ten degrees off the normal axis in the longitudinal direction, with the offset axis of each opening in a paired set being turned toward the other opening in the paired set.

SUMMARY OF THE INVENTION

The invention in various embodiments is a rib fixation system comprising an elongated bone plate and mono-cortical bone screws received within screw-receiving openings in the bone plate, the bone screws being of sufficient length to pass through the bone plate and through the anterior or ventral cortex of the rib bone, wherein the bone screws are of a length such that they pass through the anterior cortex but not the posterior cortex of the rib, yet provide sufficient affixation of the bone plate to the rib.

The screw-receiving openings are positioned and oriented as paired sets, wherein the axis of each of the bores of the openings in a paired set are offset from the axis normal to the surface of the bone plate. The offset axis of each opening is angled approximately ten degrees from the normal axis in the transverse direction toward the longitudinal midline of the bone plate and is also angled approximately ten degrees off the normal axis in the longitudinal direction. For a paired set of openings, the deviation in the longitudinal direction of the offset axis of a first opening in a paired set is in the direction toward the second opening in the paired set, and the deviation in the longitudinal direction of the offset axis of the second opening is in the direction of the first opening. This orientation of the axes within the paired set of openings results in the bone screws being "toed-in" when inserted through the bone plate. The openings in each paired set are offset from the longitudinal midline of the elongated bone plate on opposite sides of the midline, such that a first longitudinal row of openings is partially or completely superior to the midline and a second longitudinal row of openings is partially or completely inferior to the midline.

The bone plates may be flat but are preferably curved in one or more of the longitudinal, transverse or normal axes. Most preferably the screw-receiving openings comprise a main bore, generally cylindrical, and an exterior countersunk bore of greater diameter than the diameter of the main bore. This structure allows the surgeon to place a bone screw within an opening in an off-axis manner to avoid a fracture line, weak or diseased area of bone, etc.

In alternative terminology, the invention is a rib fixation system comprising an elongated bone plate; paired sets of screw-receiving openings disposed in said bone plate; and bone screws disposed in said screw-receiving openings; wherein for each of said paired sets of screw-receiving openings, said bone screws disposed in said screw-receiving openings are angled toward each other. Additionally, such rib fixation system wherein said elongated bone plate has a longitudinal midline, and for each of said paired sets of screw-receiving openings, said screw-receiving openings are disposed on opposite sides of said midline; wherein for each of said paired sets of screw-receiving openings, said bone screws disposed in said screw-receiving openings are angled toward said midline; wherein for each of said paired sets of screw-receiving openings, said bone screws disposed in said screw-receiving openings are angled approximately ten degrees toward each other and are angled approximately ten degrees toward said midline; and/or wherein said screw-receiving openings comprise countersunk bores.

Alternatively, a rib fixation system comprising an elongated bone plate having a longitudinal midline, an anterior surface and a posterior surface; paired sets of screw-receiving openings disposed in said bone plate, wherein for each of said paired sets of screw-receiving openings, one of said screw-receiving openings is a superior opening disposed superior to said midline and the other of said screw-receiving openings is an inferior opening disposed inferior to said midline; said superior opening having a superior normal axis perpendicular to said bone plate at the location of said superior opening, said superior normal axis being a reference axis, and a superior offset axis that is angled toward said midline approximately ten degrees from said superior normal axis, said superior offset axis defining the true axis of said superior opening, and said inferior opening having an inferior normal axis perpendicular to said bone plate at the location of said inferior opening, said inferior normal axis being a reference axis, and an inferior offset axis that is angled toward said midline approximately ten degrees from an axis normal to said bone plate at the location of said inferior opening, said inferior offset axis defining the true axis of said inferior opening; said superior offset axis of said superior opening also being angled approximately ten degrees from said superior normal axis in the direction toward said inferior opening, and said inferior offset axis of said inferior opening also being angled approximately ten degrees from inferior normal axis in the direction toward said superior opening; and bone screws disposed in said screw-receiving openings; wherein for each of said paired sets of screw-receiving openings, said bone screws disposed in said screw-receiving openings are angled toward each other and toward said midline. Furthermore, such a system wherein said screw-receiving openings comprise countersunk bores disposed on said anterior surface of said bone plate; wherein said countersunk bores are sized so as to allow said bone screws to be disposed in said superior and said inferior openings only substantially coaxially with said superior and said inferior offset axes; wherein said countersunk bores are sized so as to allow said bone screws to be disposed in said superior openings and said inferior openings non-coaxially with said superior and said inferior offset axes; wherein said superior normal axes and said inferior normal axes are defined at said anterior surface of said bone plate; wherein said superior normal axes and said inferior normal axes are defined at said posterior surface of said bone plate; wherein said superior openings are disposed longitudinally along said bone plate in a superior row and said inferior openings are disposed longitudinally along said bone plate in an inferior row; and/or wherein for each said paired set of screw-receiving apertures said superior opening and said inferior opening are offset longitudinally along said bone plate.

Also alternatively, a rib fixation system comprising an elongated bone plate having a longitudinal midline, a convex anterior surface and a concave posterior surface, the curvature of said posterior surface substantially matching the curvature of the anterior surface, said bone plate being curved in the longitudinal direction; paired sets of screw-receiving openings disposed in said bone plate, wherein for each of said paired sets of screw-receiving openings, one of said screw-receiving openings is a superior opening disposed superior to said midline and the other of said screw-receiving openings is an inferior opening disposed inferior to said midline; said superior opening having a superior normal axis perpendicular to said bone plate at the location of said superior opening, said superior normal axis being a reference axis, and a superior offset axis that is angled toward said midline approximately ten degrees from said superior normal axis, said superior offset axis defining the true axis of said superior opening, and said inferior opening having an inferior normal axis perpendicular to said bone plate at the location of said inferior opening, said inferior normal axis being a reference axis, and an inferior offset axis that is angled toward said midline approximately ten degrees from an axis normal to said bone plate at the location of said inferior opening, said inferior offset axis defining the true axis of said inferior opening; said superior offset axis of said superior opening also being angled approximately ten degrees from said superior normal axis in the direction toward said inferior opening, and said inferior offset axis of said inferior opening also being angled approximately ten degrees from inferior normal axis in the direction toward said superior opening; said screw-receiving openings comprising countersunk bores disposed on said anterior surface of said bone plate; and bone screws disposed in said screw-receiving openings and recessed within said countersunk bores; wherein for each of said paired sets of screw-receiving openings, said bone screws disposed in said screw-receiving openings are angled toward each other and toward said midline. Furthermore, such a system wherein said bone screws disposed in said superior openings are coaxially aligned with said superior offset axes and said bone screws disposed in said inferior openings are coaxially aligned with said inferior openings; and/or wherein said bone screws are chosen such that said bones screws disposed in said superior openings may be disposed out of alignment with said superior offset axes and said bones screws disposed in said inferior openings may be disposed out of alignment with said inferior offset axes.

DETAILED DESCRIPTION OF THE INVENTION

With reference to the drawings, the invention in various embodiments will now be described, the drawings meant to be representative and illustrative but not limiting as to the possible variations and embodiments. The terms of direction used herein, such as anterior and posterior, shall be taken as in reference to the human body, i.e., the terms anterior or ventral shall mean the direction to the front or forward exterior of the chest area and the term posterior shall mean the direction toward the back or rearward exterior of the chest area. For three-dimensional space, the X axis shall be the direction laterally across the human body, i.e., side-to-side, the Y axis shall be the superior-inferior direction of the human body, i.e., head-to-toe, and the Z axis shall be direction anterior-posterior direction, i.e., front to back. Thus, the ribs and preferred embodiment of the rib plates will extend longitudinally in the X direction with curvature in the Z direction to correlate to the major long curve of the rib. The anterior surface of the ribs possess a transverse convex surface curvature in the Y direction and at least the posterior, i.e. interior, surface of the preferred embodiments of the rib plates will possess a transverse concave curve in the Y direction. Most preferably, the anterior, i.e., exterior, surface of the rib plates will approximate or match the curvature of the posterior surface of the rib plate so as to possess a transverse convex surface.

The term midline is used herein to refer to the longitudinal midline of the rib plate. The term normal axis is used herein to mean a line passing through a point that is normal, i.e., perpendicular, to the plane tangent to the surface of the rib plate at the point—the anterior surface when the anterior surface matches the posterior surface, and the posterior surface when the surfaces differ and the posterior surface better correlates to the anterior surface of a rib. The term offset axis is used herein to mean the true axis of the screw-receiving openings that is angled from the normal axis, i.e., the offset axis defines the bore to receive and direct the bone screw, such that the axis of the bone screw is substantially coaxial to the offset axis when the screw is inserted. Thus, the normal axis is defined at the location of the screw-receiving opening and serves as a referential axis, while the offset axis defines the true axis of the bore of the screw-receiving opening. The term toed-in is used herein to mean that for bones screws positioned in a paired set of screw-receiving openings, the two bone screws will not be disposed in parallel planes, but instead will angle in toward each other in the X axis direction and toward the midline in the Y axis direction. The term mono-cortical as used herein means the length of the bone screws and direction of insertion into the rib is such that when the bone plate is affixed to the rib the bone screw passes through the anterior cortex but does not pass through the posterior cortex.

The rib or bone plates 10 and the bone screws 23, mechanical fasteners also referred to as cortical screws, for affixing the bone plates to a rib 31 may be composed of any suitable material that is bio-compatible for surgical implantation into the human body, such as for example titanium, and which possess sufficient rigidity to support the rib. The bone plates 10 are preferably malleable or bendable to a limited degree such that a surgeon may bend the bone plates 10 to better conform to the particular rib 31 to which it is being attached.

Figure 1:
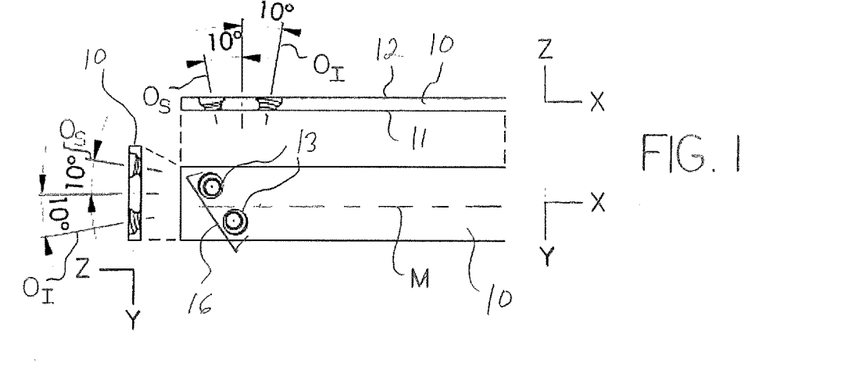
FIG. 1 is an illustration of an embodiment of the invention showing a flat bone plate with flat, parallel inner and outer surfaces.

FIG. 1 illustrates a basic embodiment of the bone plate 10 shown in multiple axes, the bone plate 10 being an elongated bar-shaped, flat body, rectangular in cross-section, having plural paired sets 16 of screw-receiving openings 13 (only one paired set 16 being shown in the figure). The openings 13 define bores adapted to receive bone screws 23 for affixation of the bone plate 10 to a rib 31. In the paired set 16, one opening 13 is disposed at a point superior to the midline M of the bone plate 10 and the other opening 13 is disposed at a point inferior to the midline M and shifted longitudinally in the X direction from the superior opening 13. Each opening 13 of the paired set 16 possesses an offset axis O, referred to herein as $O_S$ for an opening 13 in a superior row 14 and $O_I$ for an opening 13 in an inferior row 15. The offset axis $O_S$ for an opening 13 is angled or tilted approximately 10 degrees toward the midline M of the rib plate 10 from the direction normal or perpendicular to the anterior surface 12 or posterior surface 11 of the rib plate 10. Likewise, the offset axis $O_I$ for an opening 13 is angled or tilted approximately ten degrees toward the midline M of the rib plate 10 from the direction normal or perpendicular to the anterior surface 12 or posterior surface 11 of the rib plate 10. In other words, the two openings 13 of the paired set 16, and by this design the bone screws 23 received by the openings 13, are not disposed in parallel planes but instead are angled superiorly (upward) and inferiorly (downward) respectively in the Y direction. Furthermore, the offset axis $O_S$ for a superior opening 13 in a paired set 16 is tilted or angled approximately ten degrees in the X direction toward the paired inferior opening from the direction normal or perpendicular to the anterior surface 12 or posterior surface 11 of the rib plate 10, and the offset axis $O_I$ of the inferior openings 13 in a paired set 16 is tilted or angled approximately ten degrees in the X direction toward the paired superior opening from the direction normal or perpendicular to the anterior surface 12 or posterior surface 11 of the rib plate 10. In this manner, bone screws 23 inserted into the openings 13 of a paired set 16 will be substantially coaxially aligned with the offset axes O and will angle toward the midline and toward each other. This toed-in or barbed disposition better secures the bone plate 10 to the rib 31 to resist separation of the bone plate 10 over time or under high stress.

Figure 2:
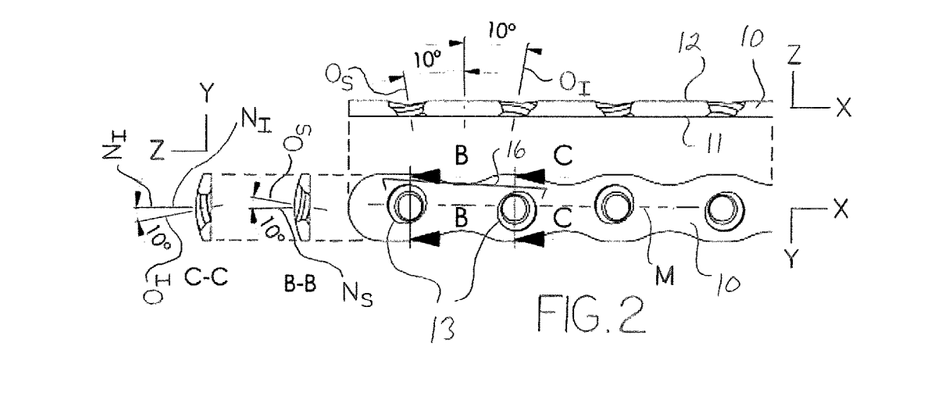
FIG. 2 is an illustration of an alternate embodiment of the invention showing flat bone plate with a flat inner surface and a curved outer surface.
Figure 3:
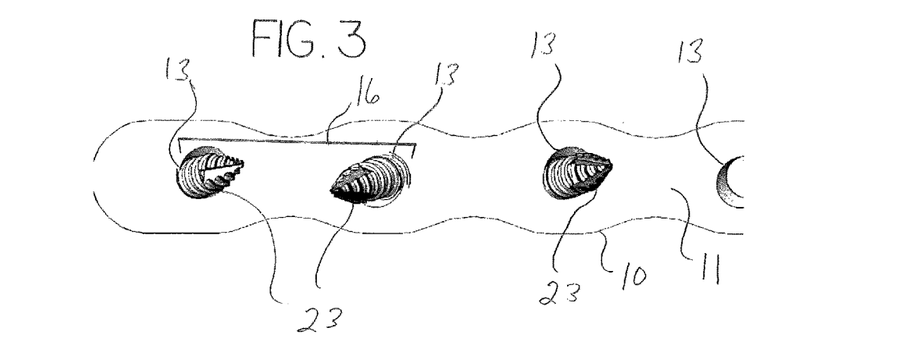
FIG. 3 is a view of the inner surface of a bone plate of the type shown in FIG. 2 wherein bone screws have been positioned in some of the screw-receiving openings.

FIGS. 2 and 3 illustrate an embodiment of a bone plate 10 wherein the openings 13 are disposed closely adjacent the midline M. As with FIG. 1, the offset axes $O_S$ of the openings 13 in the superior row 14 are offset approximately ten degrees in the X direction and the Y direction from the normal axis $N_S$ and the offset axes $O_I$ of the openings 13 in the inferior row 15 are offset approximately ten degrees in the X direction and the Y direction, with the offset axes $O_S$ and $O_I$ of each of the paired sets 16 being angled toward each other and toward the midline M.

Figure 4:
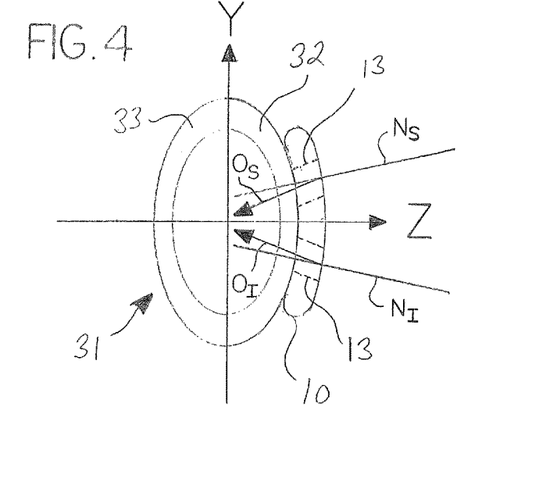
FIG. 4 is an illustration showing a bone plate curved in the transverse direction with a superior opening and an inferior opening, and further illustrating the offset axis relative to the normal axis for each opening.
Figure 5:
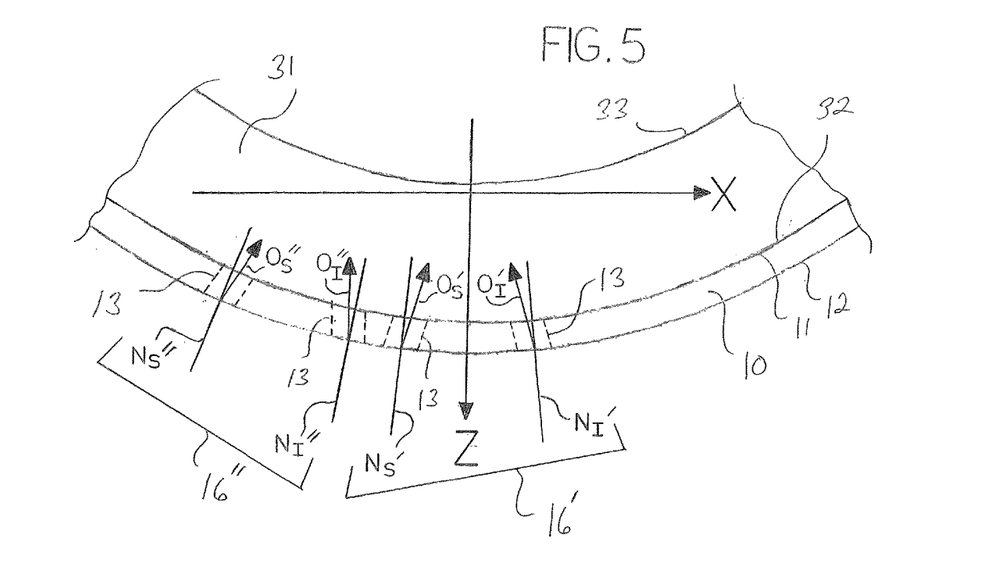
FIG. 5 is an illustration showing a bone plate curved in the longitudinal direction with a first superior opening and a first inferior opening forming a first paired set and a second superior opening and a second inferior opening forming a second paired set, and further illustrating that the offset axis relative to the normal axis for each opening in a paired set is directed toward the other offset axis.
Figure 6:
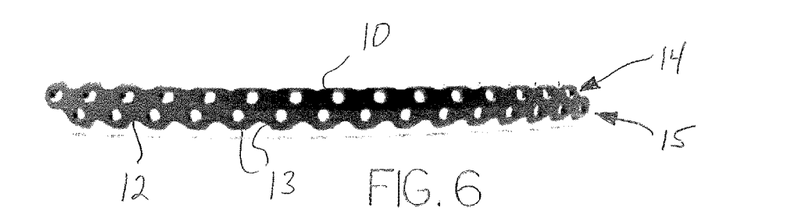
FIG. 6 is an illustration showing the outer surface of a curved bone plate.
Figure 7:
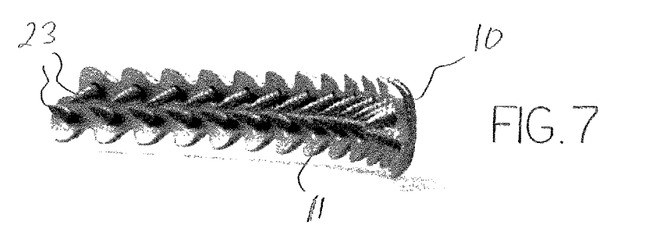
FIG. 7 is an illustration of the inner surface of the bone plate of FIG. 6 with bone screws inserted into the openings.
Figure 8:
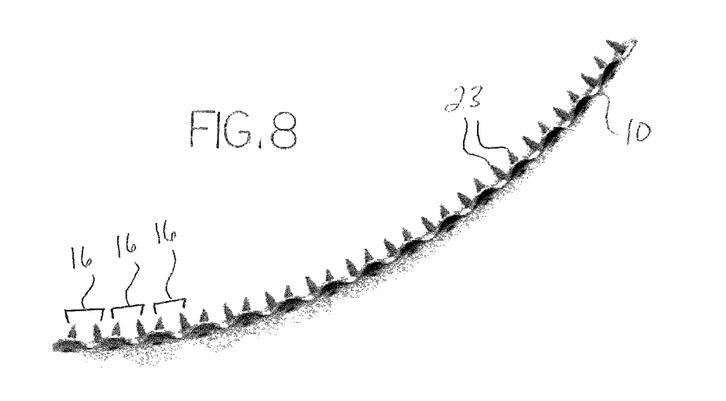
FIG. 8 is an illustration of the edge of the bone plate of FIG. 7.
Figure 9:
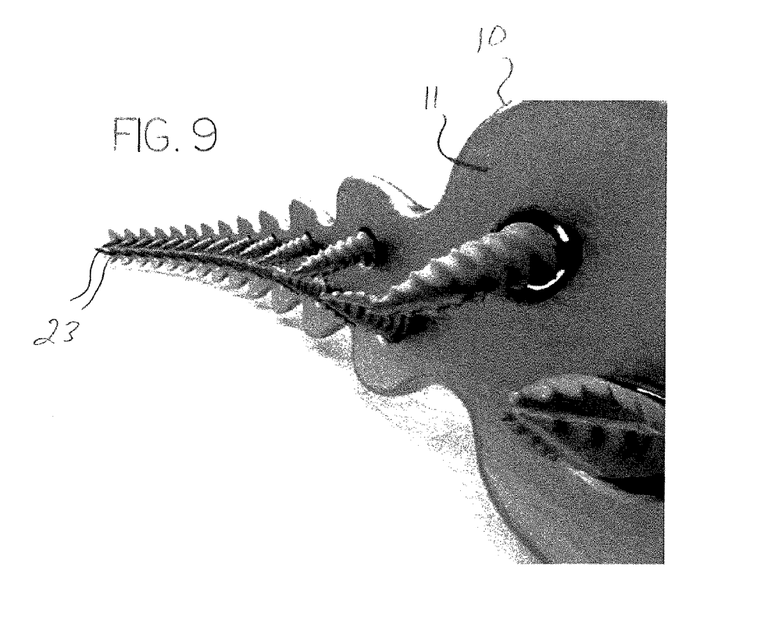
FIG. 9 is a close-up illustration of a portion of the bone plate of FIG. 7.
Figure 10:
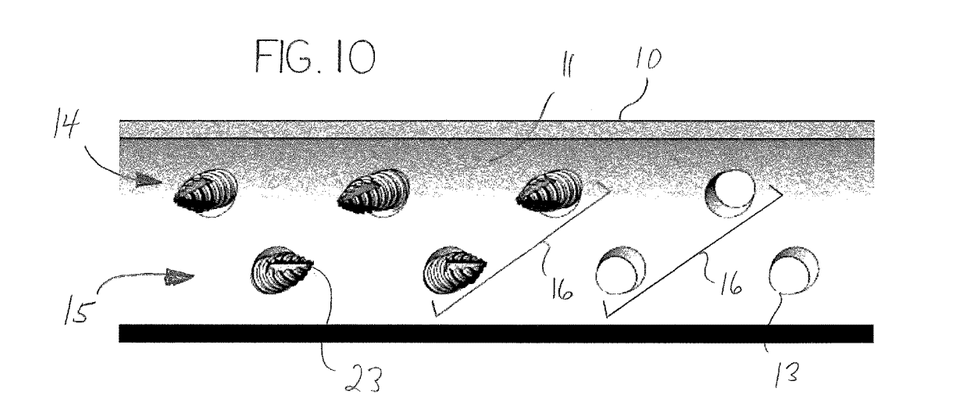
FIG. 10 is an illustration of the inner surface of a bone plate showing superior and inferior rows of openings and paired sets of openings.
Figure 11:
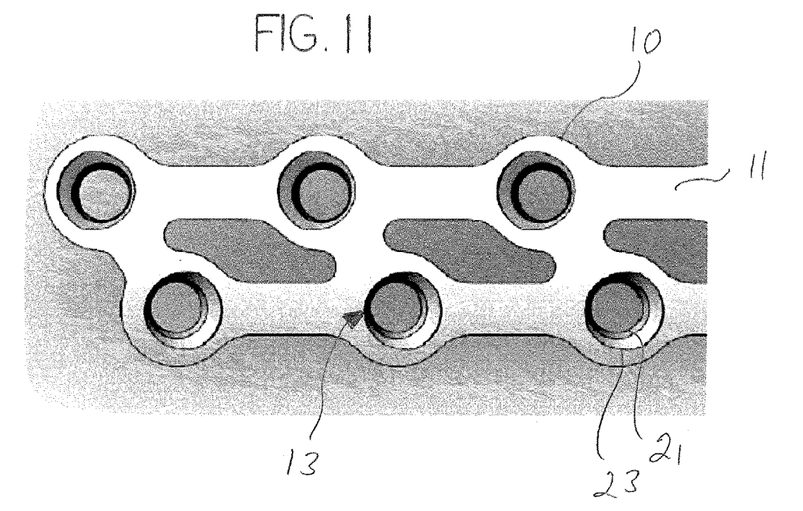
FIGS. 11 through 14 show various embodiments for the bone plates.
Figure 12:
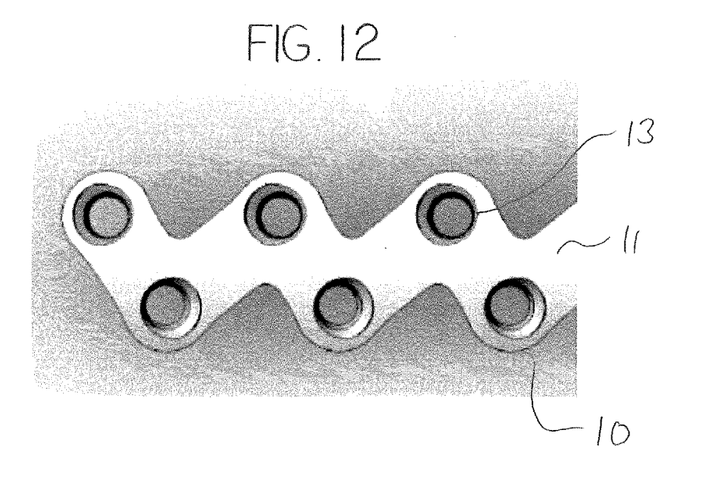
Figure 13:
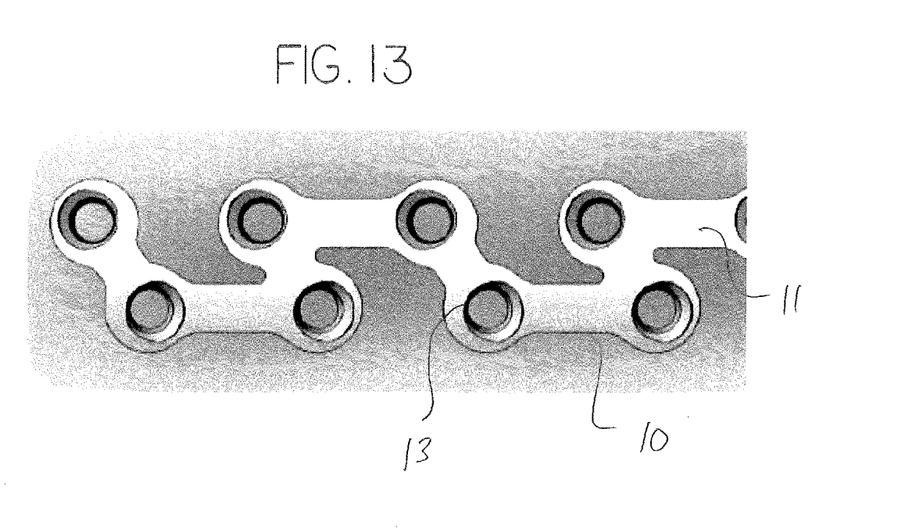
Figure 14:
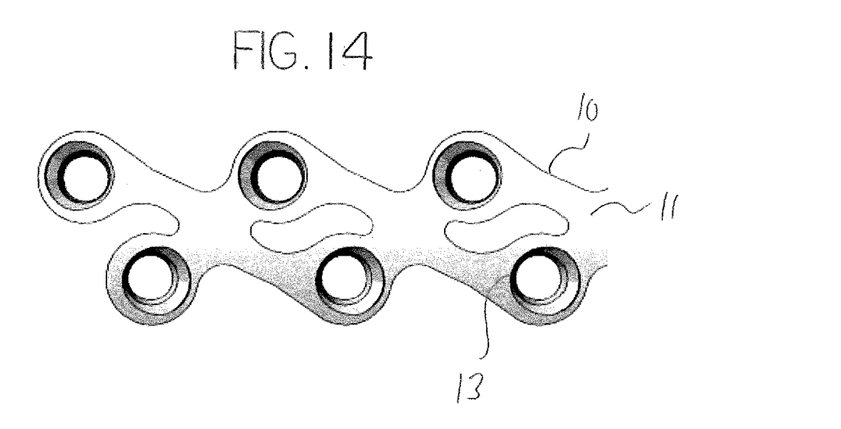

FIGS. 4 through 10 illustrate a more preferred embodiment of the bone plate 10, wherein the bone plate 10 is curved longitudinally in the X direction and curved transversely in the Y direction, with the anterior surface 12 substantially matching the curvature of the posterior surface 11. The longitudinal and transverse curvature of the bone plate 10 provides a configuration that is more likely to match the curvature of the rib 32, thereby requiring little or no shape manipulation by the surgeon for optimum affixation. As shown in FIG. 4, the offset axis $O_S$ of the superior opening 13 is angled approximately ten degrees from the normal axis $N_S$ in the inferior direction and the offset axis $O_I$ of the inferior opening 13 is angled approximately ten degrees from the normal axis $N_I$ in the superior direction. Bone screws 23 of proper length inserted into the two openings 13 will pass through the anterior cortex 32 but not pass through the posterior cortex 33 of the rib 31. Two paired sets 16' and 16" are shown in FIG. 5. For paired set 16', the offset axis $O_S'$ of superior opening 13 is angled approximately ten degrees in the X direction from the normal axis $N_S'$ in the direction toward the inferior opening 13 of the paired set 16', and the offset angle $O_I'$ of the inferior opening 13 is angles approximately ten degrees in the X direction from the normal axis $N_I'$ in the direction toward the superior opening 13 of the paired set 16'. Likewise, for paired set 16", the offset axis $O_S''$ of superior opening 13 is angled approximately ten degrees in the X direction from the normal axis $N_S''$ in the direction toward the inferior opening 13 of the paired set 16", and the offset angle $O_R''$ of the inferior opening 13 is angles approximately ten degrees in the X direction from the normal axis $N_I''$ in the direction toward the superior opening 13 of the paired set 16". As seen in FIGS. 7 through 10, this structure results in paired sets of bone screws 23 that are toed-in or barbed. The bone screws 23 will not make contact with each other.

FIGS. 11 through 14 illustrate other embodiments for the bone plate 10, wherein portions of the body material of composition is removed in order to lighten the bone plates 10 and reduce material costs, the removed portions being chosen along the edges and in the interior such that structural integrity and rigidity are not detrimentally reduced and the bone plate 10 remains suitable for its intended purpose.

Figure 15:
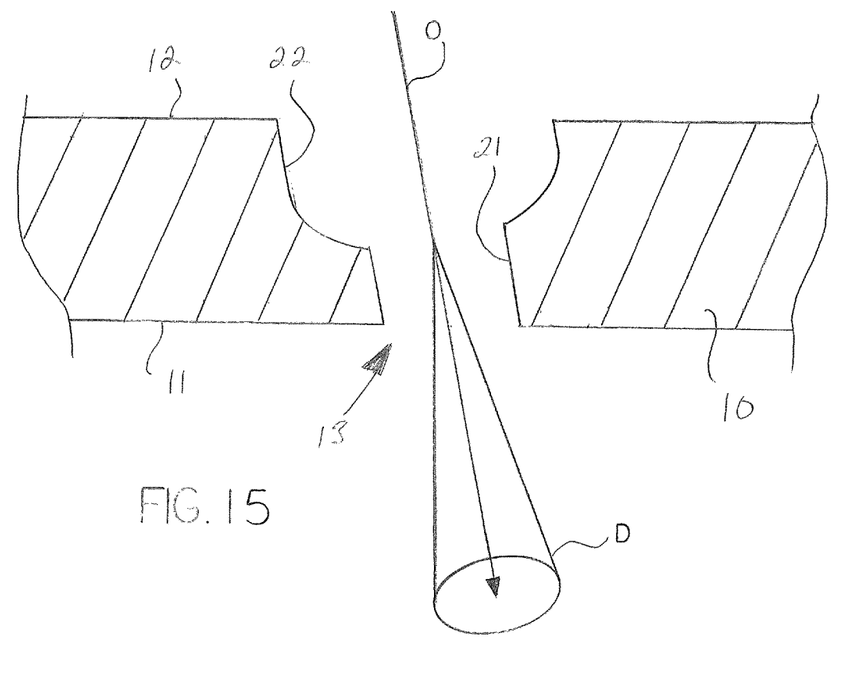
FIG. 15 illustrates the cone of deviation for placement of the bone screw resulting from the provision of a countersunk bore in the opening.

In another embodiment illustrated in FIG. 15, the openings 13 are provided with countersunk bores 22, such that the opening 13 comprises a main bore 23 of a first diameter and a countersunk bore 22 of second and greater diameter. This configuration allows the heads of the bone screws 23 to be recessed to present a smoother exterior surface. Alternatively, if the heads of the bone screws 23 are chosen to be significantly smaller in diameter than the diameter of the countersunk bore 22, the true placement axis of the bone screw 23 may vary slightly from the offset axis O, such that the placement axis may fall within a conical deviation zone D as shown in FIG. 15. In other words, the bone screw 23 may be pivoted or tilted slightly away from the offset axis O. With this combination of properly chosen bone screws 23 and countersunk bores 22 on the anterior surface 12 of the bone plate 10, the surgeon may alter the placement axis of the bone screws 23 if needed to avoid fracture lines, weak or diseased portions of the rib 31, etc.

It is understood that equivalents and substitutions for certain elements set forth and illustrated above may be obvious to hose of skill in the art, and therefore the true scope and definition of the invention in its various embodiments is to be as set forth in the following claims.

We claim:

1. A rib fixation system comprising:
an elongated bone plate having a longitudinal midline, an anterior surface and a posterior surface;
paired sets of screw-receiving openings disposed in said bone plate, wherein for each of said paired sets of screw-receiving openings, one of said screw-receiving openings is a superior opening disposed superior to said midline and the other of said screw-receiving openings is an inferior opening disposed inferior to said midline;
wherein for each said paired set of screw-receiving openings, said superior opening and said inferior opening are offset longitudinally along said bone plate;
said superior opening having a superior normal axis perpendicular to said bone plate at the location of said superior opening, said superior normal axis being a reference axis, and a superior offset axis that is angled toward said midline approximately ten degrees from said superior normal axis, said superior offset axis defining the true axis of said superior opening, and said inferior opening having an inferior normal axis perpendicular to said bone plate at the location of said inferior opening, said inferior normal axis being a reference axis, and an inferior offset axis that is angled toward said midline approximately ten degrees from an axis normal to said bone plate at the location of said inferior opening, said inferior offset axis defining the true axis of said inferior opening;
said superior offset axis of said superior opening also being angled approximately ten degrees from said superior normal axis in the direction toward said inferior opening, and said inferior offset axis of said inferior opening also being angled approximately ten degrees from inferior normal axis in the direction toward said superior opening; and
mono-cortical bone screws disposed in said screw-receiving openings;
wherein for each of said paired sets of screw-receiving openings, said bone screws disposed in said screw-receiving openings are angled toward each other and toward said midline, and are not aligned on a single plane.

2. The system of claim 1, wherein said screw-receiving openings comprise countersunk bores disposed on said anterior surface of said bone plate.

3. The system of claim 2, wherein said countersunk bores are sized so as to allow said bone screws to be disposed in said superior and said inferior openings only substantially coaxially with said superior and said inferior offset axes.

4. The system of claim 2, wherein said countersunk bores are sized so as to allow said bone screws to be disposed in said superior openings and said inferior openings non-coaxially with said superior and said inferior offset axes.

5. The system of claim 1, wherein said superior normal axes and said inferior normal axes are defined at said anterior surface of said bone plate.

6. The system of claim 1, wherein said superior normal axes and said inferior normal axes are defined at said posterior surface of said bone plate.

7. The system of claim 1, wherein said superior openings are disposed longitudinally along said bone plate in a superior row and said inferior openings are disposed longitudinally along said bone plate in an inferior row.

8. A rib fixation system comprising:
an elongated bone plate having a longitudinal midline, a convex anterior surface and a concave posterior surface, the curvature of said posterior surface substantially matching the curvature of the anterior surface, said bone plate being curved in the longitudinal direction;
paired sets of screw-receiving openings disposed in said bone plate, wherein for each of said paired sets of screw-receiving openings, one of said screw-receiving openings is a superior opening disposed superior to said midline and the other of said screw-receiving openings is an inferior opening disposed inferior to said midline;
wherein for each said paired set of screw-receiving openings said superior opening and said inferior opening are offset longitudinally along said bone plate;
said superior opening having a superior normal axis perpendicular to said bone plate at the location of said superior opening, said superior normal axis being a reference axis, and a superior offset axis that is angled toward said midline approximately ten degrees from said superior normal axis, said superior offset axis defining the true axis of said superior opening, and said inferior opening having an inferior normal axis perpendicular to said bone plate at the location of said inferior opening, said inferior normal axis being a reference axis, and an inferior offset axis that is angled toward said midline approximately ten degrees from an axis normal to said bone plate at the location of said inferior opening, said inferior offset axis defining the true axis of said inferior opening;
said superior offset axis of said superior opening also being angled approximately ten degrees from said superior normal axis in the direction toward said inferior opening, and said inferior offset axis of said inferior opening also being angled approximately ten degrees from inferior normal axis in the direction toward said superior opening;

said screw-receiving openings comprising countersunk bores disposed on said anterior surface of said bone plate; and mono-cortical bone screws disposed in said screw-receiving openings and recessed within said countersunk bores;

wherein for each of said paired sets of screw-receiving openings, said bone screws disposed in said screw-receiving openings are angled toward each other and toward said midline, and are not aligned on a single plane.

9. The system of claim 8, wherein said bone screws disposed in said superior openings are coaxially aligned with said superior offset axes and said bone screws disposed in said inferior openings are coaxially aligned with said inferior openings.

10. The system of claim 8, wherein said bone screws are chosen such that said bones screws disposed in said superior openings may be disposed out of alignment with said superior offset axes and said bones screws disposed in said inferior openings may be disposed out of alignment with said inferior offset axes.

* * * * *